United States Patent [19]

Wright

[11] 3,998,556
[45] Dec. 21, 1976

[54] COLOR CONTRAST GAUGE

[75] Inventor: Robert V. Wright, Cloquet, Minn.

[73] Assignee: Potlatch Corporation, San Francisco, Calif.

[22] Filed: June 23, 1975

[21] Appl. No.: 589,359

[52] U.S. Cl. .............................. 356/186; 35/28.3; 356/191; 356/194
[51] Int. Cl.[2] ........................................ G01J 3/48
[58] Field of Search ............ 35/28.3; 356/173, 186, 356/189, 191–194

[56] References Cited
UNITED STATES PATENTS

| | | | |
|---|---|---|---|
| 2,027,816 | 1/1936 | Drucker | 356/192 X |
| 3,436,157 | 4/1969 | Adler et al. | 356/192 |

*Primary Examiner*—John K. Corbin
*Assistant Examiner*—F. L. Evans
*Attorney, Agent, or Firm*—Merchant, Gould, Smith, Edell, Welter & Schmidt

[57] ABSTRACT

A color contrast gauge to determine and test the proper contrast of a light background to a darker machine-readable symbol printed thereon.

3 Claims, 4 Drawing Figures

U.S. Patent  Dec. 21, 1976  3,998,556
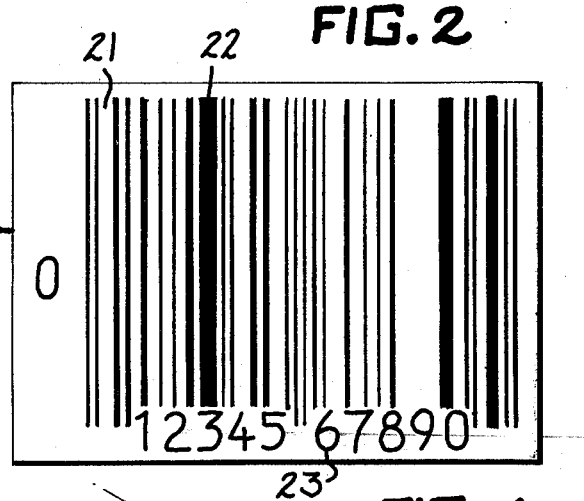
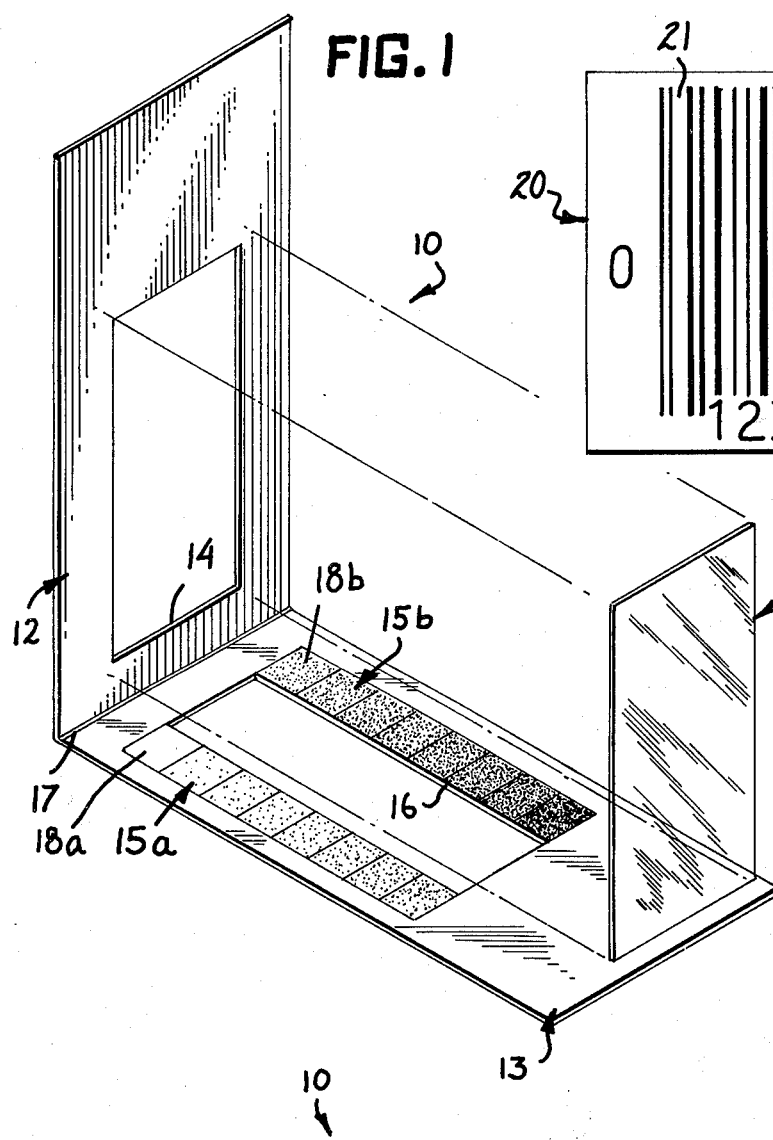
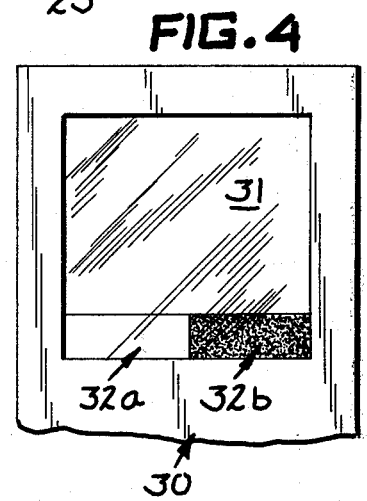

COLOR CONTRAST GAUGE

BACKGROUND OF THE INVENTION

1. Field of the Invention

This invention generally concerns a device for determination of the proper contrast between a background substratum and darker symbols printed thereon, and more specifically concerns a device to assure the proper contrast of a light background to dark symbol bars printed thereon for Universal Product Codes symbols during artwork preparation and production of packaging material which utilize the Universal Product Codes.

Statement of the Problem

In recent years, several new consumer marketing systems have been developed to provide, inter alia, computer-assisted item pricing and inventory management. One such system, currently utilized by the food and drug industry, uses Universal Product Codes (U.P.C.) symbols which are a series of light and dark bar-like symbols of varying width and which are printed on the package or wrapper of consumer goods. These symbols are machine-readable by utilizing a photosensitive scanner which is responsive to the variation in symbol width printed on the package. The coded symbols represent information regarding the product manufacturer and a description of that particular product.

When the coded symbols are "read" by the scanner, the information is "interpreted" by computer. The computer is generally programmed to provide pricing and inventory information regarding each product.

The Universal Product Code Council has set specifications for this machine-readable symbol in the U.P.C. Symbol Specification Manual. Producers of grocery and drug packaging materials are required to print the symbols to these specifications, and producers of the photosensitive scanners are required to produce machines which will read the symbols printed to these specifications.

One of the specifications of the U.P.C. Symbol Specification Manual gives the required color density for the dark bars or symbols as a function of the light background upon which they are printed. This is to ensure uniformity throughout the U.P.C. system as an improper contrast between the background and the printed symbols will prevent the scanner from obtaining an accurate signal. To provide this uniformity, the manual requires that all print contrast signal measurements are to be made using equipment equivalent to the Kidder Optical Character Tester, Model 082 with a Wratten 26 filter and a 0.008 inch aperture. This particular type of equipment is very expensive (costs range from $2,500.00 to $3,000.00) and is cumbersome to use. Therefore, a simple method and device for approximating the same contrast measurement was needed.

SUMMARY OF THE INVENTION

The present invention achieves the need for a reasonably accurate, economical, and simple device for determining and testing a symbol color scheme for proper U.P.C. print contrast signal requirements.

The invention includes a paperboard frame having a window therein. The window includes an optical gelatin filter and graduated color scales beneath the window respectively corresponding to tolerable colors for packaging background substratum and the dark code bars printed thereon.

BRIEF DESCRIPTION OF THE DRAWINGS

FIG. 1 is an exploded elevational view of a first embodiment of the present invention;

FIG. 2 is a representative view of a typical U.P.C. symbol;

FIG. 3 is an elevational view of an embodiment of the present invention with a typical U.P.C. symbol as it would appear in use; and FIG. 4 is an elevational view, partly in section, of a second embodiment of the present invention.

Detailed Description of the Drawings

Referring now to FIG. 1, there is shown generally a first embodiment of the color contrast gauge 10. Color contrast gauge 10 is formed of a paperboard frame having an upper portion 12 and a lower portion 13. Formed in the upper portion 12 of the frame is a window opening 14 and positioned within the lower portion 13 of the frame is a corresponding window opening 16. Upper portion 12 and lower portion 13 of the frame are foldable along crease 17 or can be formed from two separate pieces. Positioned between upper portion 12 and lower portion 13 of the frame, within the window opening formed therein is an optical gelatin filter 11. Filter 11 can be a Kodak Wratten Gelatin Filter No. 26 or any suitable equivalent thereof. Secured to the lower portion 13 of the frame, or printed thereon, is a bottom graduated color scale 15a and a top graduated color scale 15b. Bottom scale 15a and top scale 15b are positioned such that when upper portion 12 of the frame is in alignment with portion 13 they will be at least partially visible through window opening 14 in the upper portion 12 of the frame. Filter 11 is positioned between upper portion 12 and lower portion 13 of the frame and when folded into place it will be on top of color scales 15a and 15b and beneath upper portion 12 of the frame. The upper portion 12 and lower portion 13 of the frame can be bonded together by glue or any other suitable means. The color scales 15a and 15b are printed as follows. A range of suitable background colors are selected and are arranged on the scale from lightest to darkest. From this background scale a suitable color for code symbol bars can be determined by reference to the requirements of the Universal Product Code Symbol Specification Manual. The manual provides the print contrast signal requirements in the form of color density values and reflectance values required for printing suitable symbol bars in relation to corresponding background color values. That is, for each background color on the light scale, a requisite symbol bar color is determined and then printed on the opposite scale from lightest to darkest. The scales are printed so that the symbol bar color is oppositely disposed from the background color. For example, the background color, 18a on scale 15a of FIG. 1, has a color density value when viewed through the filter of 0.075. In order to meet the requirements of the U.P.C. Symbol Specification Manual, the symbol bar color to be used with such background must have a color density of at least 0.495 when determined through the filter. Therefore, color 18b in scale 15b of FIG. 1 would have a color density of .495 plus any desired safety factor, for example 0.15, so that any symbol bar which is as dark or darker than the color identified by 18b would meet the requirements of the U.P.C. It would also be possible to reverse the procedure and start with selected colors for the symbol bars and then, by reference to the manual, determine the color density requirement for a suitable background for each preselected symbol bar color. Similarly, the colors on each of the scales could be printed in reverse, that is, from darkest to lightest. The Universal Product Code Symbol Specification Manual is currently available through Distribution Codes, Inc., of Alexandria, Virginia. Color samples for use in preparation of the color scales are commercially available and can be obtained from the Pantone Color Specifier or similar commercial products.

Referring now to FIG. 3, there is shown the first embodiment of the color contrast gauge 10 as it would appear in use. Color contrast gauge 10 is positioned over code symbol 20 with the bars of code symbol 20 visible through filter 11. Lower scale 15a and upper scale 15b are shown in relationship to code symbol 20 as they would appear during performance of the contrast test.

Referring now to FIG. 4, a second embodiment 30 of the color contrast gauge is shown. Filter 31 is fabricated of the same material as filter 11 of FIG. 1. Whereas the first embodiment of the color contrast gauge 10 included graduated color scales 15a and 15b, the second embodiment of the color contrast gauge 30 includes only two color scales, 32a and 32b. Color scale 32a corresponds generally to the standard light background material which is used in the majority of folding cartons and which often serve as a background for graphics and the U.P.C. symbols. Scale 32a is solid bleached sulfate clay coated paperboard. The second scale 32b is a color scale which has a color density of 0.65 when viewed through a Wratten Filter No. 26. This is the minimum dark bar density as determined by the U.P.C. Symbol Specification Manual plus an 0.15 safety factor. The safety factor is used to provide for variable conditions during manufacture resulting in marginal values.

Operation

There are two embodiments of the present invention. One embodiment, as is generally described in FIG. 4 utilizes two color scales. One scale, as stated previously, uses a regular solid bleach sulfate clay coated paperboard such as is used for the majority of folding cartons and which often serves as a background for graphics and the U.P.C. symbols. The second scale is a color scale which has a color density through a Wratten 26 filter of 0.165. To use this embodiment of the gauge in determining whether a color meets the U.P.C. print contrast signal requirements (color contrast), these steps are involved:

1. Place the color contrast gauge flat (in contact) over the color sample;
2. The light background or substratum should be equal to or lighter than the light color standard when viewed through the Wratten 26 filter;
3. The color for the dark bars of the symbol should be equal to or darker than the color standard when viewed through the red filter.

The print contrast signal, as referred to above, is defined by the equation:

$$PCS = (R_L\% - R_D\%) \div R_L\%$$

where $R_L$ - percent reflectance of the "light" background and where $R_D$ equals percent reflectance of the dark "bars". All reflectance measurements referred to are relative to 100% reflectance as determined with $MgO$ or $BaSO_4$ and zero percent reflectance as determined with a "black cavity" as per U.P.C. requirements.

Another embodiment of the present invention, as is generally described in FIG. 1, uses the same principle but instead has multiple graduated color scales for contrasting the light background and dark bars. This embodiment is intended for use on packages and wrappers where the background or substratum has a color or color density equal to or darker than the standard U.P.C. paperboard. The color scales are selected to correspond to the specifications of the U.P.C. Symbol Specification Manual in table 5. The following table provides a range of requisite values for density of the color scales. A safety factor of 0.13 density was obtained by adding 0.13 to the dark bar density corresponding to the light background.

Table I

| Light Bars | Dark Bars | | | | |
|---|---|---|---|---|---|
| Density | Density | + Safety | = | New Density | Actual Density |
| .07 | .49 | .13 | | .62 | .61 |
| .13 | .63 | .13 | | .76 | .75 |
| .19 | .82 | .13 | | .95 | .95 |
| .26 | .98 | .13 | | 1.11 | 1.09 |
| .34 | 1.20 | .13 | | 1.33 | 1.33 |
| .39 | 1.32 | .13 | | 1.45 | 1.44 |
| .43 | 1.40 | .13 | | 1.53 | 1.58 |
| .50 | 1.60 | .13 | | 1.73 | 1.74 |

In this embodiment, the lower color scale 15a and the upper color scale 15b are aligned such that the minimum tolerances of contrast of the light background to the dark bars are positioned directly above and beneath each other. In using this embodiment of the color contrast gauge to perform the contrast test, the following steps are involved:

1. Lay the color contrast gauge flat over the color background sample;
2. Match the color sample on the lighter color scale to the closest background color for the symbol as both are viewed through the filter;
3. The symbol bar color should be equal to or darker than the color scale sample directly above the lower background color scale as viewed through the filter.

In this embodiment of the color contrast gauge a 0.13 safety factor is included. Further, this embodiment of the color contrast gauge can also be used in the reverse direction by first matching the symbol bar color desired on the upper symbol color scale and then finding the corresponding maximum background color on the background color scale directly below.

While the present invention is best adaptable for use with the U.P.C. system, it is not limited to that system. Other similar systems could be used with the present invention by modifying the filter and/or color scales upon variation of signal contrast requirements.

What is claimed is:
1. A color contrast gauge, comprising:
   a. a substantially flat frame having a window opening formed therein;
   b. a predetermined optical filter arranged within said window opening being integrally bonded to said frame; and c. at least one predetermined color scale visible through said filter in which at least one color of said color scale is a predetermined light color, and another color is a predetermined dark color, said color scale being affixed to and carried by said frame.

2. A color contrast gauge, comprising:
a. a substantially flat frame having a window opening formed therein;
b. a predetermined optical filter arranged within said window being integrally bonded to said frame; and
c. a color scale visible through said filter comprising two sections; a light color section and a dark color section, each section comprising a plurality of color portions with each portion varying in density; each light color portion having a related color portion in the dark color section, the relationship between each light color portion and its related dark color portion being such that when the light color portion corresponds to a pre-selected background color then the density of a color symbol bar to be printed on said background color must be as dark as or darker than the dark color portion.

3. A color contrast gauge, comprising:
a. a substantially flat frame having a window opening formed therein;
b. a predetermined optical filter arranged within said window being integrally bonded to said frame; and
c. a color scale visible through said filter comprising a light portion and a dark portion and said light portion is formed of a solid bleached sulfate clay coated paperboard and said dark portion has a color density of 0.65 when viewed through said filter.

* * * * *